(12) United States Patent
Fahl

(10) Patent No.: US 9,458,100 B2
(45) Date of Patent: *Oct. 4, 2016

(54) SYNTHESIS AND GROWTH REGULATORY ACTIVITY OF A PROTOTYPE MEMBER OF A NEW FAMILY OF AMINOTHIOL RADIOPROTECTORS

(71) Applicant: Wisconsin Alumni Research Foundation, Madison, WI (US)

(72) Inventor: William E. Fahl, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/957,188

(22) Filed: Aug. 1, 2013

(65) Prior Publication Data

US 2014/0107217 A1    Apr. 17, 2014

Related U.S. Application Data

(60) Provisional application No. 61/713,050, filed on Oct. 12, 2012.

(51) Int. Cl.
*A01N 33/08* (2006.01)
*A61K 31/13* (2006.01)
*C07C 323/25* (2006.01)

(52) U.S. Cl.
CPC ............. *C07C 323/25* (2013.01); *A61K 31/13* (2013.01)

(58) Field of Classification Search
None
See application file for complete search history.

(56) References Cited

U.S. PATENT DOCUMENTS 7,314,959 B2 *   1/2008  Fahl et al. .................... 564/512

OTHER PUBLICATIONS

Copp et al. "Radioprotective effi cacy and toxicity of a new family of aminothiol analogs." International Journal of Radiation Biology 2013, pp. 1-8.
Copp et al. "Synthesis and Growth Regulatory Activity of a Prototype Member of a New Family of Aminothiol Radioprotectors." Bioorg Med Chem Lett. Dec. 15, 2011; 21(24): 7426-7430.
Peebles et al., "ROS-Scavenger and Radioprotective Efficacy of the New PrC-210 Aminothiol." Radiation Research 2012, 178:57-68.
Soref et al. "A New Orally Active, Aminothiol Radioprotector-Free of Nausea and Hypotension Side Effects at Its Highest Radioprotective Doses." International Journal of Radiation Oncology 2011, e702-e707.

* cited by examiner

*Primary Examiner* — Jared Barsky
(74) *Attorney, Agent, or Firm* — Daniel A. Blasiole; Joseph T. Leone, Esq.; Dewitt Ross & Stevens SC

(57) ABSTRACT

The synthesis, growth inhibition and radioprotective activity of the PrC-210 aminothiol, 3-(methyl-amino)-2-((methyl-amino)methyl)propane-1-thiol, and its polyamine and thiolated polyamine progenitors are reported. All of the molecules significantly inhibited growth of cultured normal human fibroblasts. The combination of an ROS-scavenging thiol group and a positively charged alkyl-amine backbone provided the most radioprotective aminothiol molecule.

14 Claims, 12 Drawing Sheets

SYNTHESIS AND GROWTH REGULATORY ACTIVITY OF A PROTOTYPE MEMBER OF A NEW FAMILY OF AMINOTHIOL RADIOPROTECTORS

This application claims priority to U.S. Pat. Appl. Ser. No. 61/713,050, which is incorporated herein by reference in its entirety.

FIELD OF INVENTION

Provided herein is technology related to the synthesis, growth inhibition, and radioprotective activity of aminothiol compounds, e.g., 3-(methyl-amino)-2-((methylamino)methyl)propane-1-thiol (PrC-210 and the analog pRC-211), and related polyamine compounds, thiolated polyamine compounds, and progenitors. All of the molecules significantly inhibited growth of cultured normal human fibroblasts. The combination of an ROS-scavenging thiol group and a positively charged alkyl-amine backbone provided the most radioprotective aminothiol molecule.

BACKGROUND OF THE INVENTION

Radiotherapy-induced dermatitis is a common side effect seen in up to 85% of patients who receive a course of radiotherapy as part of their cancer therapy regimen. A topically administered radioprotector that could be applied prior to radiotherapy on each of the 30 irradiation days would reduce pain and long term scarring and would improve patient compliance in receiving all days of treatment. Skipped radiotherapy days have a discernible risk for the patient as measured by a decrease in 5 year survival rate for breast cancer.

OBJECTS AND SUMMARY OF THE INVENTION

There is also a need for new systemically administered radioprotectors (see, e.g., Examples 2, 3, 4, 6, and 7) that lack the side effects of nausea/vomiting (see, e.g., Example 4) and hypotension/fainting (see, e.g., Example 5) that have hampered the use of current generation aminothiol radioprotectors, most notably the five carbon aminothiophosphonate, amifostine. The aminothiol radioprotector design concepts of: (i) a flexible alkyl chain backbone, which carries a positive charge due to one or more amine groups, to achieve ionic interaction and concentration around negatively charged DNA in cells, and (ii) the presence of a free or capped thiol group to scavenge oxygen free radicals formed from ionizing radiation, have been used before in programs to build radioprotective molecules within both the U.S. and the former Soviet Union.

In the present investigation, we disclose a process in which: (i) the number of alkylamine segments in the aminothiol backbone is systematically increased to increase drug-DNA affinity and ionic interaction, resulting in increased growth inhibition that is associated with this enhanced drug-DNA interaction, and (ii) the placement or 'display' of a free thiol reactive oxygen species (ROS) scavenger at the end of a short alkyl side chain that displaces or 'displays' the scavenger moiety away from the DNA backbone to theoretically enable ROS scavenging before ROS attack on dG bases within cellular DNA (see, e.g., FIG. 3 and Example 7). This work has resulted in a small family of new aminothiol molecules, the prototype of which, PrC-210, is described in initial detail here.

The synthesis of PrC-210, shown in Scheme 1, started with a double displacement of chloride from 1 using N-methyl mesitylene-sulfonamide (2) and sodium hydride, to form allylic sulfonamide 3. Hydroboration of 3 afforded clean conversion to sulfonamide alcohol 4. Using standard conditions, 4 was converted to mesylate 5 which was immediately treated with potassium thioacetate to form 6. Following an established procedure, the mesitylene (Mts) protecting groups were removed with HBr/HOAc, in the presence of excess phenol. The deblocking procedure also hydrolyzed the thioacetate group. Work up resulted in a mixture of PrC-210 and the corresponding disulfide (dimer). The mixture was treated with 2-mercaptoethanol to cleave the disulfide and the product, PrC-210, was precipitated from EtOH as the HCL salt. Subsequent recrystallizations removed the sulfurous odor (see, e.g., Example 1).

The synthesis of PrC-211, shown in Scheme 2, employed a modification of the route used for PrC-210. An attempt was made to form sulfonamide 10 directly by displacement of chloride from 1 using mesitylenesulfonamide, activated with sodium hydride. A complex mixture formed, from which 10 could not be isolated in pure form. Alternatively, 1 was treated with potassium phthalimide to form allylic phthalimide 8. Removal of the phthalate groups with hydrazine provided 9, which upon treatment with mesitylenesulfonyl chloride afforded the bis-sulfonamide 10 in good yield. Using the sequence from the PrC-210 preparation, hydroboration, mesylation, thioacetate displacement and deblocking, PrC-211 was obtained as the HCl salt and subsequently recrystallized.

The amine side chains, synthesized according to the route illustrated in Scheme 3, were constructed as sulfonamide-protected intermediates, each with a single point of attachment (N—H), at one terminus, for coupling to the olefinic core (FIG. 1E). Preparations for sulfonamides 17 and 20 have previously been described. A convenient alternative approach was found that employed a modification of a reported method, starting with N-(4-bromobutyl)phthalimide (14). Displacement with N-ethyl mesitylenesulfonamide and sodium hydride, afforded 15, which upon treatment with hydrazine, was converted to 16. Amidation with mesitylenesulfonyl chloride, under standard conditions, gave 17. Sulfonamide 17, a protected diamine, represents the smallest amine side chain unit in the series, which includes 20, 21, and 22. Sulfonamide 17 was systematically elaborated to the subsequent side chain units using the same methodology as described for 17.

Coupling of the various amine side chains to the olefinic core is shown in Scheme 4. The synthesis commenced with the known TBS-protected allylic alcohol 23. Mesylation, using standard conditions, provided the activated intermediate 24. Coupling with a sulfonamide side chain and sodium hydride provided 25. Removal of the TBS-protecting groups with HCl afforded diol 26. Treatment of 26 with 1 equiv of benzoyl chloride, in the presence of pyridine, afforded alcohol 27 as a mixture of isomers. Activation of the allylic alcohol 27, for amine side chain coupling, was attempted with methanesulfonyl chloride, resulting in a complex mixture. Alternatively, the alcohol was converted to bromide 28, with phosphorous tribromide, and immediately coupled with a second side chain unit to form 29. Hydrolysis of the benzoate group was carried out under standard conditions to afford the versatile polyamine alcohol intermediate 30, which was a common intermediate for the formation of both polyamines and polyamine thiols.

Conversion of the versatile intermediate 30 to polyamines and polyamine thiols is shown in Scheme 5. Treatment of 30 with methanesulfonyl chloride and triethylamine afforded the mesylate 31. Displacement with N-ethyl mesitylenesulfonamide, activated with sodium hydride, provided 32 which was deblocked with HBr/HOAc and phenol, to afford crude polyamine 33. Free-basing with potassium carbonate followed by HCl treatment gave 33 hydrochloride salt as a mixture of cis/trans isomers. Mesylate intermediate 31 was treated with potassium thioacetate to form 34 which was de-blocked, using the same method as for 32, to form 35. Free-basing and treatment with HCl provided 35 as the hydrochloride salt.

FIG. 1A provides a summary of the first set of polyamine structures that was synthesized using the strategies outlined in Schemes 3-5. We anticipated that these drug molecules would provide radio- and chemo-protection to human cells by inducing a cell cycle block in mammalian cells at the G1/S cell cycle border because of tight binding of the (+) charged polyamine backbones to the (−) charged DNA backbone. Such a block can provide time for DNA repair in radiation- or mutagen-treated cells before washout of the polyamine drug and restoration of cell cycle progression.

FIG. 1B shows a nearly identical set of polyamines now with the addition of a thiol group to each molecule. The goal in synthesizing these molecules was to achieve the same cell cycle inhibition anticipated for the FIG. 1A molecules, but now combined with the addition of a thiol group that could serve as a scavenger for the burst of short-lived ROS that is generated when mammalian tissue is irradiated. The aminothiol and polyamine structures in FIG. 1B are growth inhibitory when added to rapidly growing, normal human fibroblasts, and the potency of growth inhibition was directly related to the number of (NH—$(CH_2)_n$) segments present within the molecule (FIG. 1D).

Early in vitro studies of radioprotection with cultured cells demonstrated that the long, polyamine structures were so growth-inhibitory (FIG. 1C) that we could not add sufficient moles of the thiolated polyamines (e.g., PrC-117) to cell cultures that would enable the thiol groups to significantly scavenge and radioprotect when the tissue culture cells were irradiated. This provided the impetus to design and synthesize the PrC-200 series of small aminothiols, of which PrC-210 is the prototype.

To determine if PrC-210 could function as a topical radioprotector that could prevent radiation dermatitis when applied prior to a cancer patient's daily radiotherapy, a rat assay that realistically mimics human radiation dermatitis was created. This assay quantifies the severity of radiation dermatitis in rat skin 13 days after a single radiation dose of 17.33 Gy. In this study, PrC-210 was applied to rat skin in an ethanol/water delivery vehicle four times in the 2 h before irradiation, and control rats received only topical vehicle before irradiation (FIG. 2). Additional drug/irradiation groups of three rats each received either the alkyl-thiol moiety or the alkyldiamine moiety from PrC-210 in the same delivery vehicle. Following the 17.33 Gy irradiation of a 1.5-3.0 cm patch of dorsal skin on the rats' backs, rats were scored 13 days later. The ability of the PrC-210 aminothiol to completely prevent radiation dermatitis was striking. Other radiodermatitis test groups exploring efficacy of thiolated polyamines or other PrC-200 series aminothiols have shown that PrC-210 is the most potent and most effective topical aminothiol to date.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 1A shows structures of first generation synthetic polyamines. FIG. 1B shows first generation 'thiolated polyamines' and the next generation aminothiol, PrC-210. FIG. 1C shows the addition of molecules at indicated concentrations to log phase, growing cultures of diploid human fibroblasts and the cell numbers measured 4 days later. FIG. 1D shows that growth inhibition is directly related to the number of [NH—$(CH_2)$] segments present in the polyamine or aminothiol molecule. FIG. 1E shows the olefinic core common to polyamine and polyamine-thiol series.

FIG. 8A shows the drugs and dosages used for the study. FIG. 8B shows recorded blood pressure after administration of amifostine. FIG. 8C shows recorded blood pressure after administration of PrC-210. FIG. 8D shows a comparison of the changes in blood pressure caused by controls (saline and epinephrine), amifostine, and PrC-210.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

EXAMPLES

Example 1

During the development of embodiments of the technology provided herein, experiments were conducted demonstrating that embodiments of the compounds provided (e.g., PrC-210) lacked noxious odors (e.g., sulfurous odors) associated with conventional compounds and technologies. Subjects were exposed to a solution comprising PrC-210 at the upper limit of what an approximate single human dose of PrC-210 is contemplated to be and a dilution series of 2-mercaptoethanol (2-ME). Each subject assigned a "smell score" to the PrC-210 by comparing the smell of the PrC-210 with the 2-ME dilutions; the smell score denotes the 2-ME dilution having a sulfurous thiol smell that most closely matched the sulfurous thiol smell of the single human dose of PrC-210. One subject assigned a smell score of 8 and the other subject assigned a smell score of 7, corresponding to 1:18,750 and 1:93,750 dilutions of 2-ME. These results show that PrC-210 at a concentration of approximately a single maximum human dose has a thiol odor that is 56,250-fold lower than 2-ME (e.g., 93,750=18,750=75,000; 75,000÷2=37,500; 37,500+18,750=56,250). A 56.250-fold dilution of 2-ME is nearly odor free.

Example 2

Figure 1:
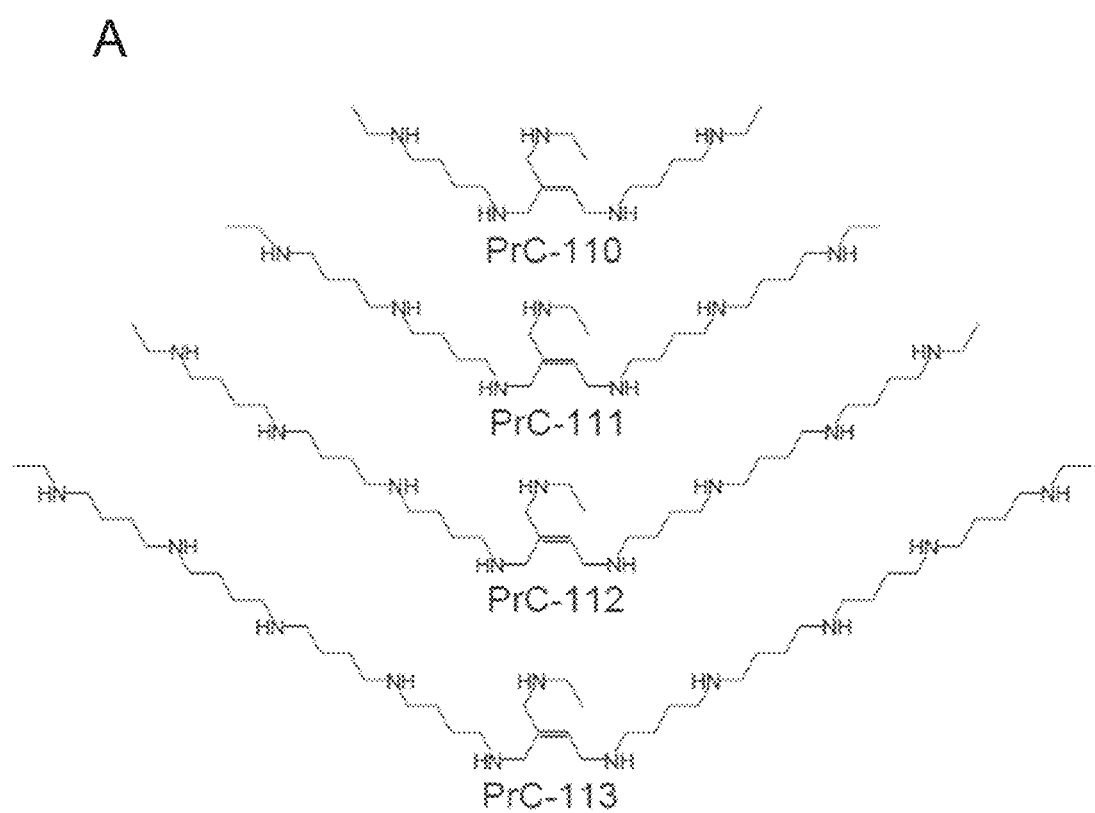
FIG. 1 shows growth inhibition of normal human cells in culture by polyamine and aminothiol molecules.
Figure 1:
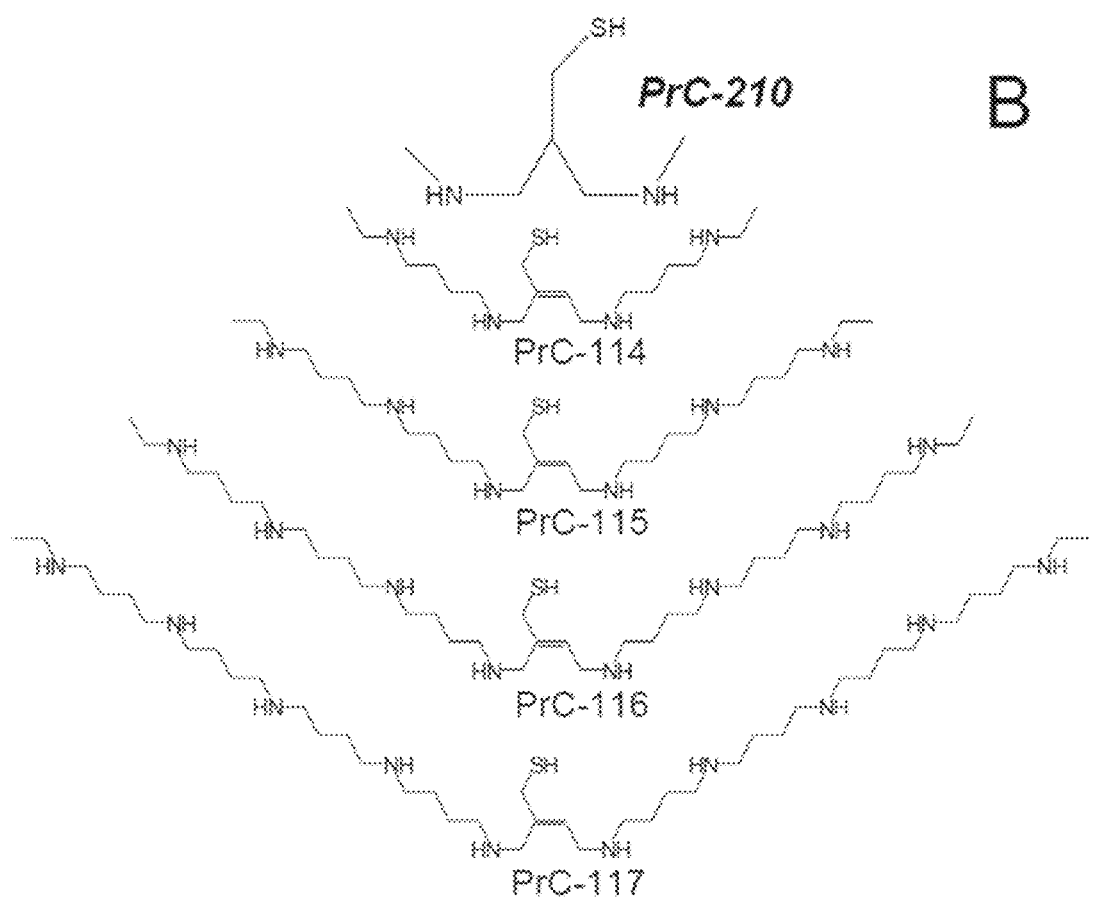
Figure 1:
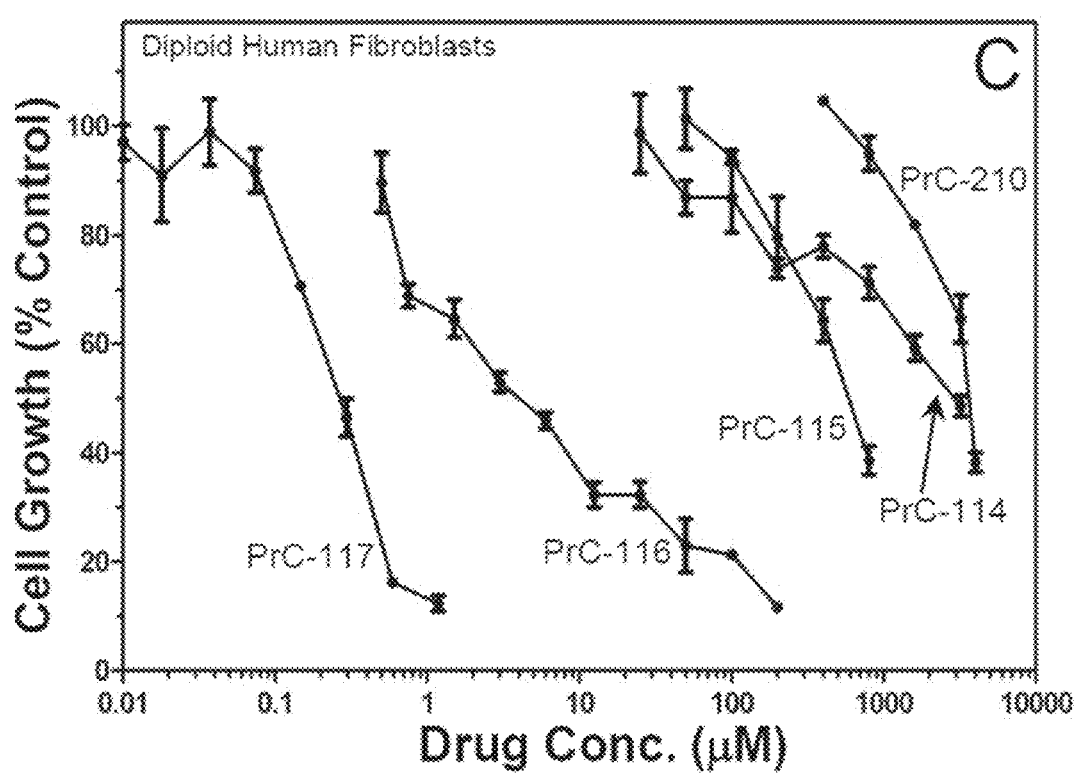
Figure 1:
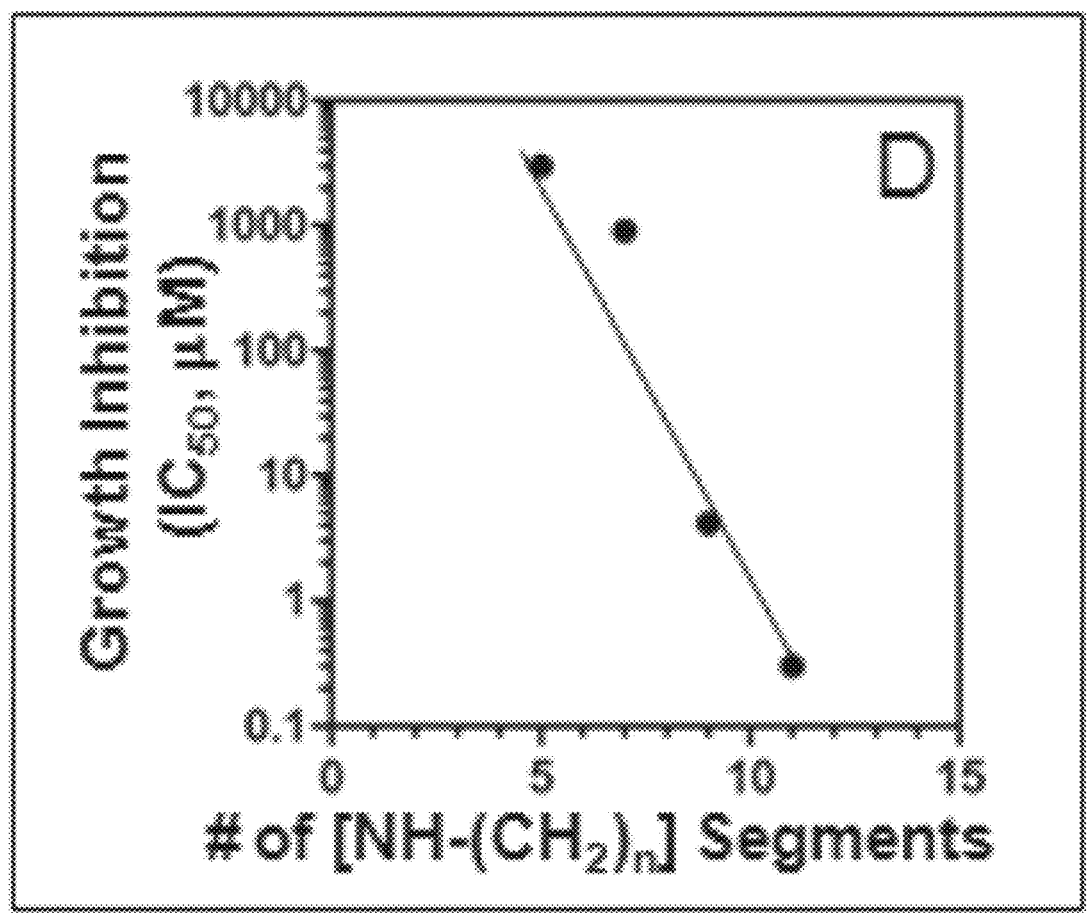
Figure 1:
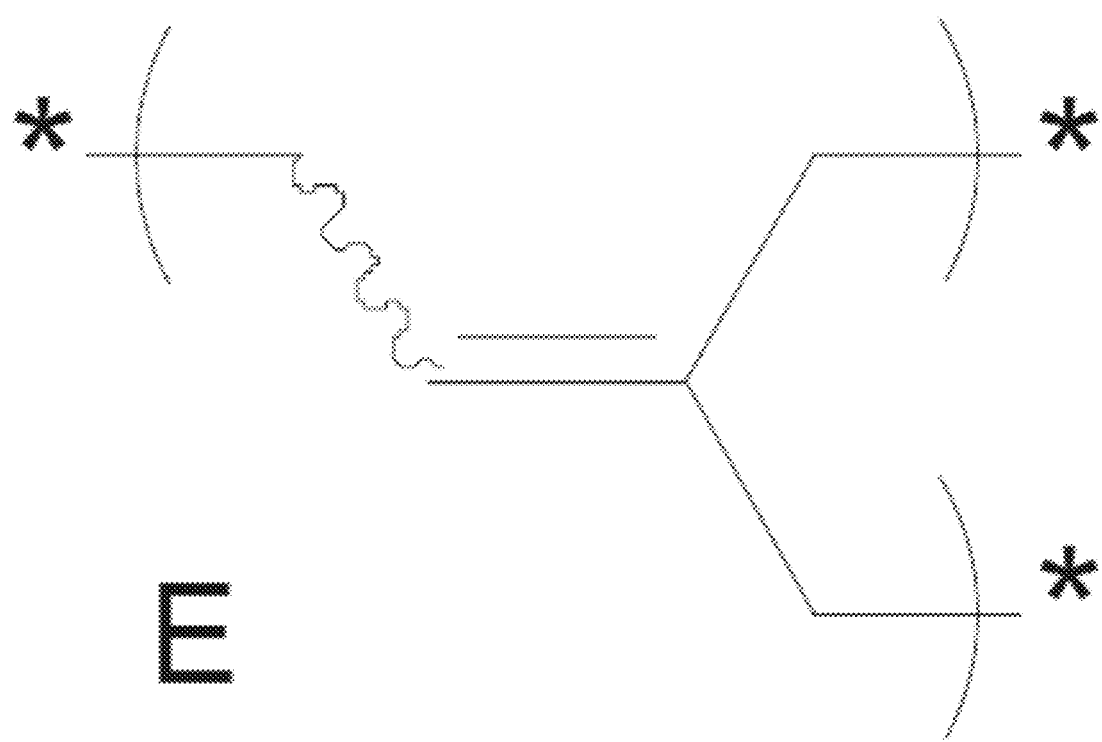
Figure 2:
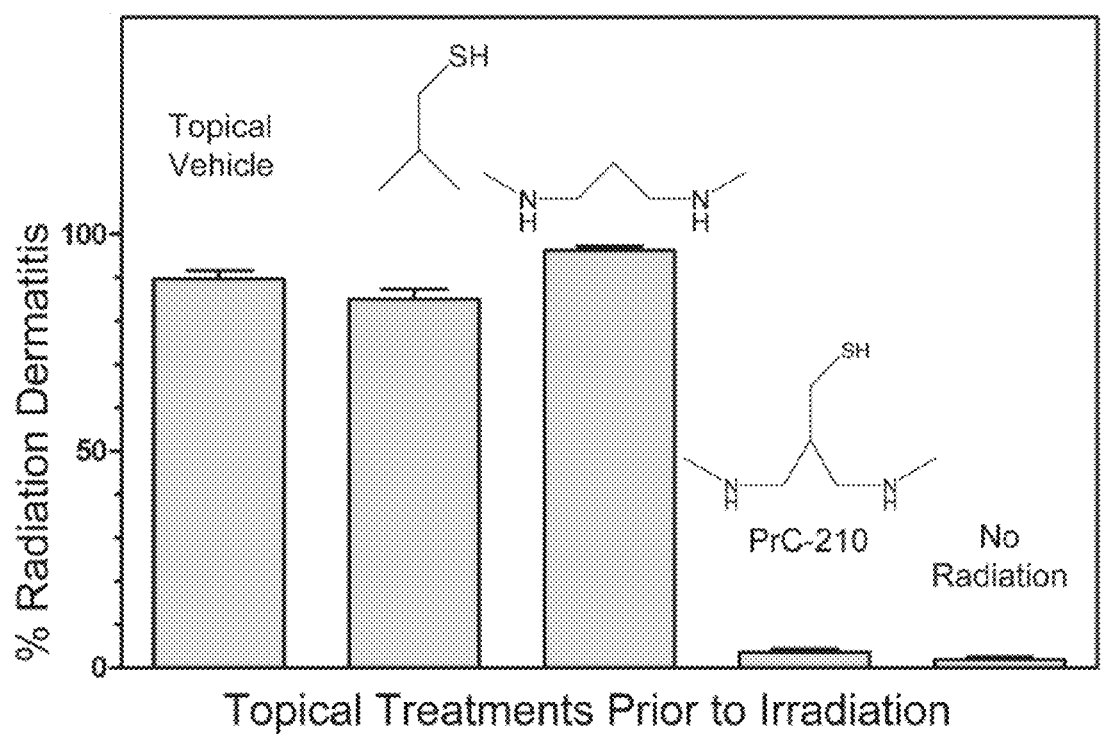
FIG. 2 shows the prevention of radiation-induced dermatitis in rat model by prior topical application of the PrC-210 aminothiol or its component structures. Molecules were applied to skin in an alcohol/water delivery vehicle prior to receiving a 17.33 Gy radiation dose to the 1.5 cm×3.0 cm skin site. Radiation dermatitis severity (e.g., % of the site covered by scab material) was scored 13 days following irradiation.
Figure 3:
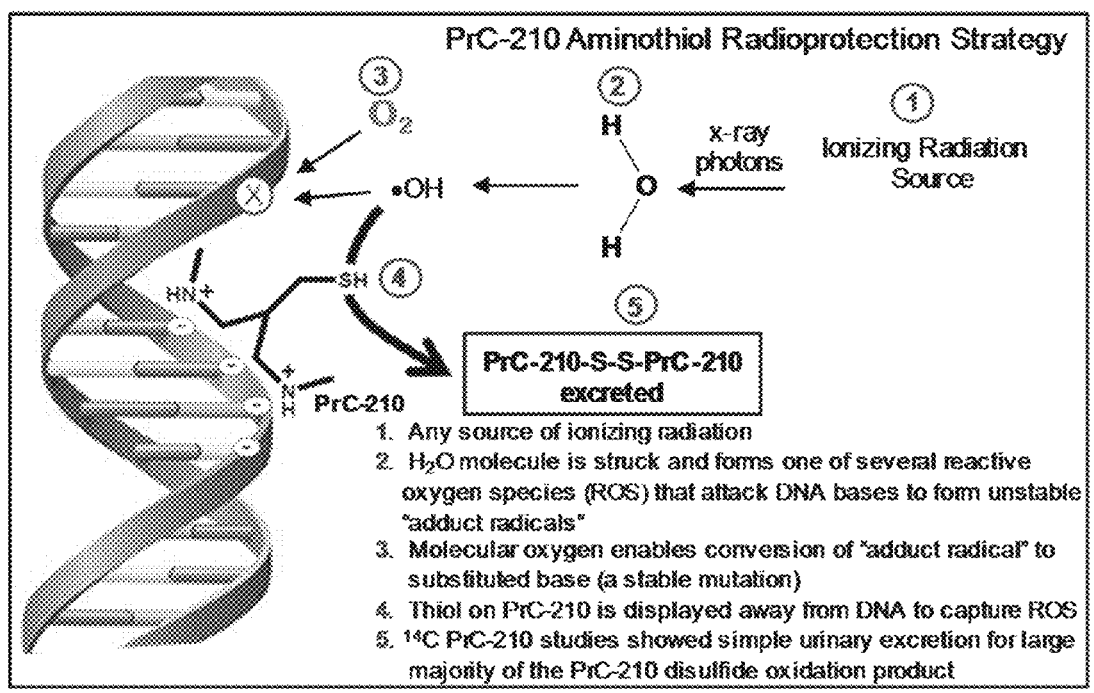
FIG. 3 shows a schematic for the contemplated mechanism of protection conferred by PrC-210 to DNA against reactive oxygen species.
Figure 4:
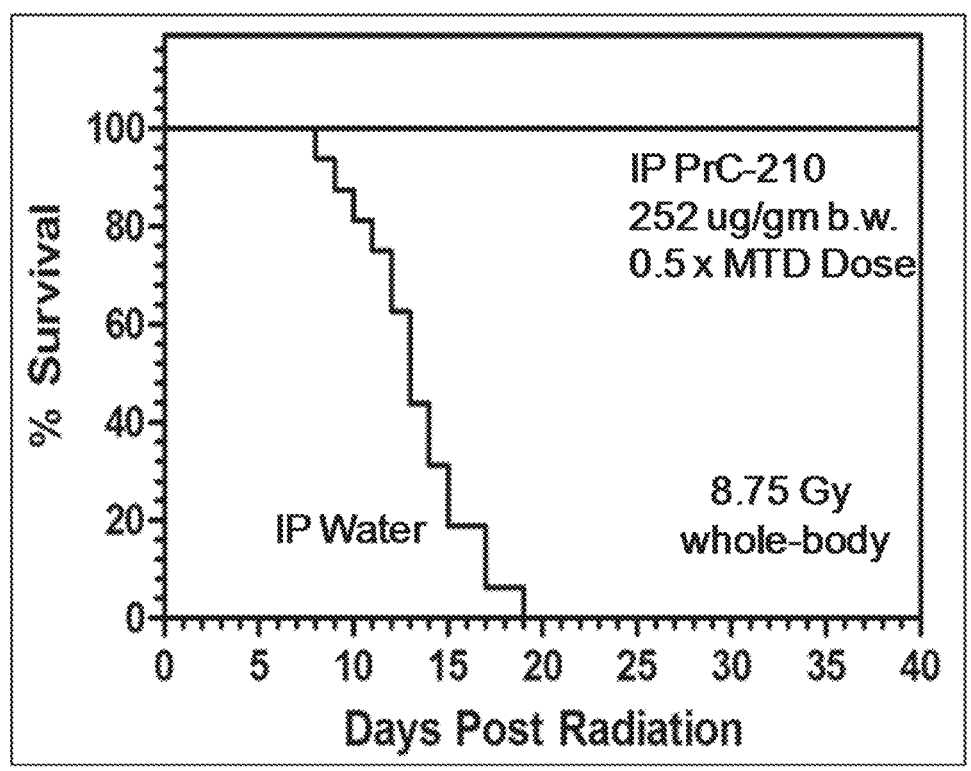
FIG. 4 shows the systemic radioprotective effect of PrC-210 in pre-exposure mouse models.

During the development of embodiments of the technology provided herein, experiments were performed demonstrating that administering an intraperitoneal, systemic dose of PrC-210 to a mouse at a time 30 minutes before exposure to 8.75 Gy of whole-body radiation confers 100% survival (FIG. 4, "IP PrC-210"). Exposure of a control mouse to the same dose of radiation in the absence of PrC-210 administration (e.g., a water-only control) is 100% lethal (FIG. 4, "IP Water"). Each treatment group contained 20 mice. The dose of PrC-210 was 252 µg/g body weight.

Example 3

Figure 5:
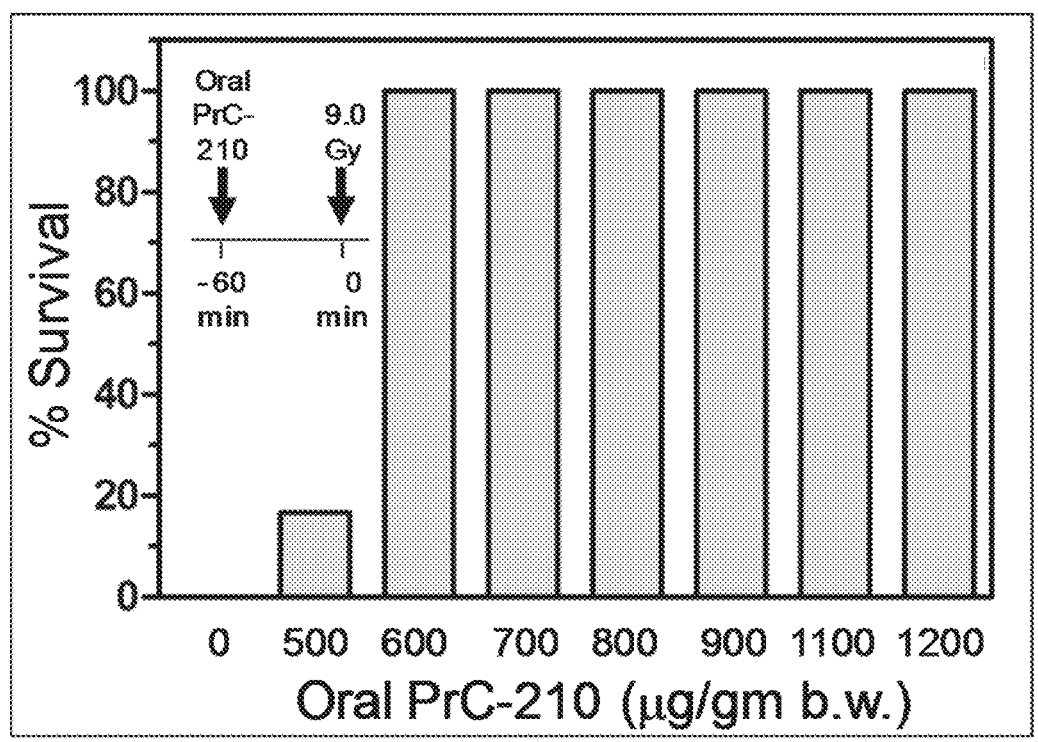
FIG. 5 shows that orally administered PrC-210 confers 100% protection against an otherwise 100% lethal dose of whole-body radiation.

During the development of embodiments of the technology provided herein, experiments were performed demonstrating that PrC-210 administered orally confers 100% protection against an otherwise 100% lethal dose of whole-body radiation. Female Sprague-Dawley rats received 200 µl doses of PrC-210 dissolved in water by gavage a time of 60 minutes prior to irradiation (time=−60 min). At time=0 min, rats were irradiated with 9.0 Gy of whole-body radiation in a $^{137}$Cs irradiator. Rats were returned to housing and their weights and survival were monitored for the next 60 days. There were six rats in each of the treatment groups. As shown by FIG. 5, oral PrC-210 confers 100% protection against an otherwise 100% lethal dose of whole-body radiation.

Figure 6:
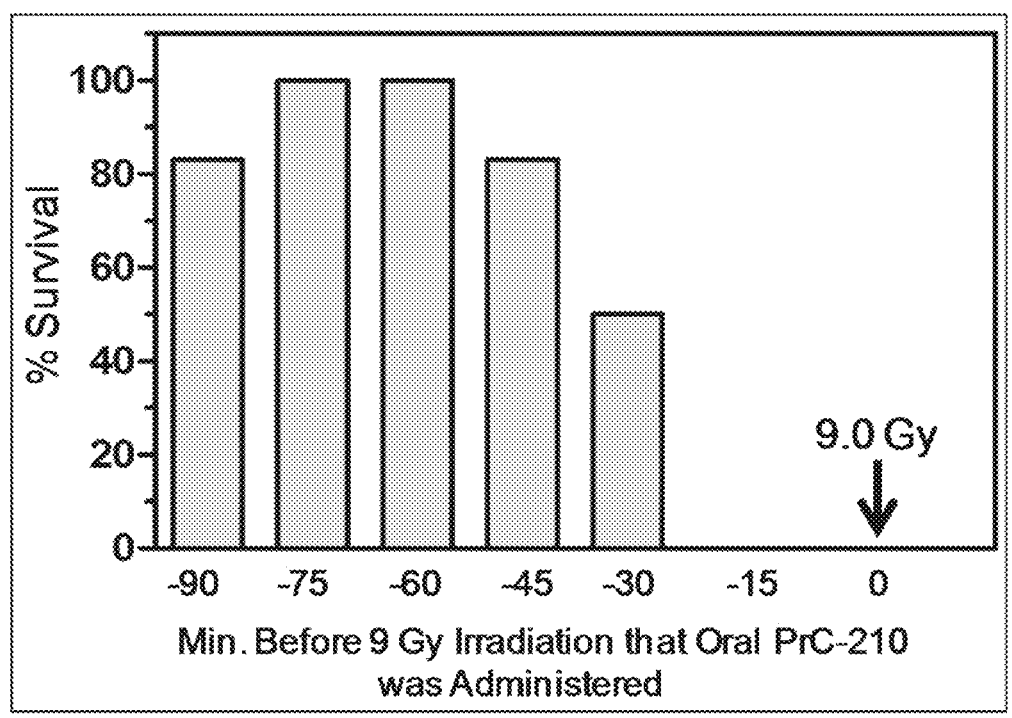
FIG. 6 shows that orally administered PrC-210 can be administered 60 minutes before irradiation to confer 100% protection against an otherwise 100% lethal dose of whole-body radiation.

In additional experiments, female ICR mice received 200 µl doses (e.g., 900 µg/g body weight) of PrC-210 dissolved in water by gavage at the indicated times prior to irradiation (See FIG. 6). At 0 min, mice were irradiated with 9.0 Gy of whole-body radiation in a $CS^{137}$ irradiator. Mice were returned to housing and their weights and survival were monitored for the next 60 days. There were six mice in each of the treatment groups. As shown in FIG. 6, the oral dose can be administered 60 minutes before irradiation and confer this effect.

Example 4

Figure 7:
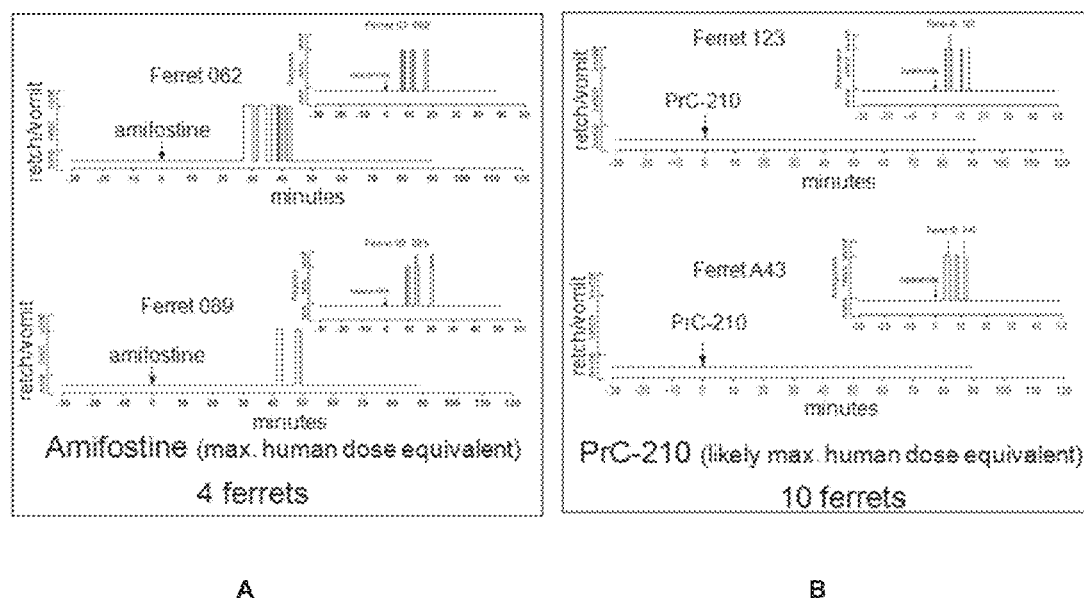
FIG. 7A shows that amifostine induces retch and emesis in a ferret model.
FIG. 7B shows that PrC-210 does not induce retch/emesis in a ferret model.

During the development of embodiments of the technology provided herein, experiments were performed demonstrating that a systemic PrC-210 dose, at the ferret equivalent of the likely highest systemic human dose that would be used, caused zero retching or emesis responses when tested in 10 ferrets (see FIG. 7B). Amifostine, at the ferret equivalent of the highest human amifostine dose used, caused retch/emesis responses in each of the four ferrets tested (FIG. 7A). Loperamide, a positive control for retch/emesis response, caused robust retch/emesis response in each of the 14 ferrets when administered 14 days after the single PrC-210 or amifostine test of the ferret.

Example 5

Figure 8:
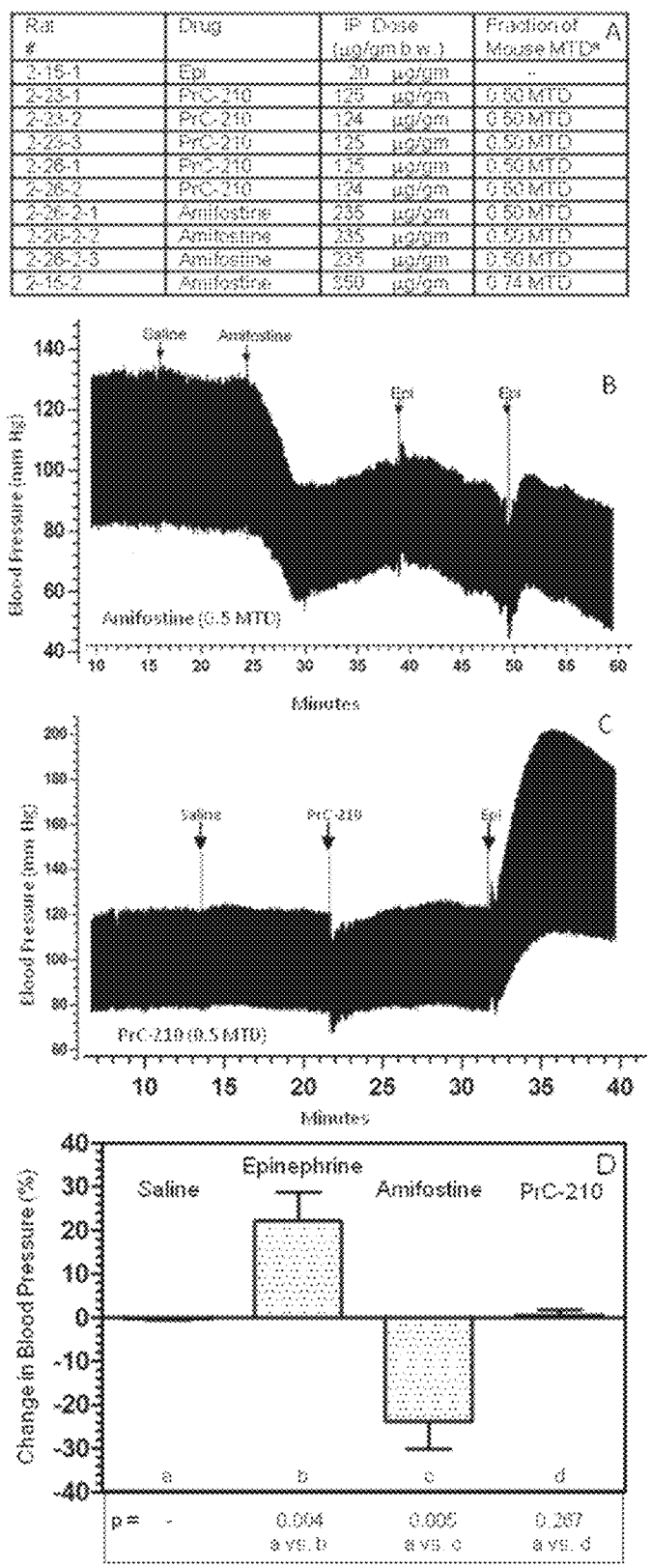
FIG. 8 shows that PrC-210 does not cause hypotension side effects.

During the development of embodiments of the technology provided herein, experiments were performed demonstrating that PrC-210 does not cause hypotension side effects caused by conventional radioprotectors (see FIG. 8). Blood pressure was monitored in the aortic artery of rats using a high-fidelity pressure transducer. Rats were continually anesthetized with 2% isofluorane, and drug doses were administered by intraperitoneal injection. Rats received intraperitoneal saline injections until these injections induced no change in monitored blood pressure. Indicated doses of PrC-210 or amifostine (FIG. 8) were administered and changes in blood pressure and heart rate were recorded. A condensed summary of drug-induced changes for all cannulated rats is shown in panel C. Doses of epinephrine (Epi; hypertensive) were also recurrently admininesterod to test if previous PrC-210 or amifostine doses could be modified.

Example 6

During the development of embodiments of the technology provided herein, experiments were conducted to test the biodistribution of an intravenous bolus dose of radiolabeled (e.g., $^{14}$C) PrC-210 in a rat host. In these experiments, an intravenous bolus of 100 µCi of $^{14}$C PrC-210 was administered into an indwelling catheter in a 300 g rat. Distribution data from this experiment are shown in Table 1;

TABLE 1

| Group | $^{14}$C PrC-210 Dose (Route) | $C_{max}$ (ng-eq/g) | $T_{max}$ (hr) | Recovery1 (excreta) | Recovery (carcass) | Recovery2 (systemic) | Recovery3 (total) |
|---|---|---|---|---|---|---|---|
| 1 | 100 uCi (IV) | 21,400 | 0.5 | 74.34% | 6.89% | 81.23% | 84.20% |

Recovery 1 (excreta) = urine + urine wipes + feces;
Recovery 2 (systemic) = Recovery (excreta) + Recovery (carcass)
Recovery 3 (total) = Recovery (systemic) + Recovery (skin) + cage wash + cage wipe + enclosure After the intravenous administration of $^{14}$C PrC-210 the main route of elimination was via urine, accounting for approximately 50% of the administered radioactivity; feces accounted for approximately 10%.

Example 7

During the development of embodiments of the technology provided herein, embodiments of compounds described herein and/or encompassed by the synthetic schemes were tested for systemic toxicity and radioprotection in mouse and rat models (Table 2). Toxic doses are shown as the "maximum tolerated dose" ("MTD") for intraperitoneal (IP), oral, and subcutaneous (SC) administration routes in Table 2.

To measure "% Survival" as a radioprotection scored endpoint, groups of 10-20 mice received the indicated drug, at the indicated dose, via the indicated delivery route, and were then exposed to a whole-body radation dose (8.75-9.0 Gy) that killed 100% of the mice in the group that received only delivery vehicle and radiation. Survival rates greater than the 0% Survival seen in the vehicle control group were attributed to systemic radioprotection conferred by the systemically administered radioprotector molecule.

TABLE 2

| Molecule Name | MW | (1) Mouse IP MTD | (2) Rat IP MTD | (3) Mouse ORAL MTD (μg/g b.w.) | (4) Rat ORAL MTD | (5) Mouse SC MTD | (6) Mouse % Survival[e] | (7) Rat % Survival[f] |
|---|---|---|---|---|---|---|---|---|
| PrC-210 | 148 | 504[a] 422[b] | 485 | 1780 | 1974 | 431 | 100% (at IP 0.5 MTD: 252 ug/g) 98% (at IP 0.5 MTD: 211 ug/g) 100% (at ORAL 0.87 MTD: 1550 ug/g)[g] | 100% (at ORAL 0.5 MTD: 900 ug/g) |
| PrC-210 Disulfide | 294 | 155 | — | — | — | — | 37% (at IP 0.9 MTD: 140 ug/g) <5% (at IP 0.5 MTD: 78 ug/g) | — |
| PrC-211 | 120 | 475 | — | — | — | — | 100% (at IP 0.9 MTD: 427 ug/g) 47% (at IP 0.5 MTD: 238 ug/g) 37% (at IP 0.25 MTD: 118 ug/g) | — |
| PrC-301 | 162 | 625 | — | — | — | — | <5% (at IP 0.5 MTD: 312 ug/g) | — |
| PrC-303 | 274 | 1860 | — | — | — | — | ND[h] | — |
| PrC-304 | 188 | 1340 | — | — | — | — | — | — |
| PrC-307 | 176 | 166 | — | — | — | — | <5% (at IP 0.5 MTD: 670 ug/g) | — |
| Amifostine | 214 | 800[c] 760[d] | — | — | — | — | 12% (at IP 0.5 MTD: 83 ug/g) 88% (at IP 0.5 MTD: 400 ug/g) | — |

[a]Determined using probit analysis of survival data
[b]Determined using best fit analysis of survival data
[c]Published value
[d]Experimentally determined
[e]8.63 Gy whole-body radiation
[f]9.5 Gy whole-body radiation
[g]This dose was the only one tested
[h]not determined As shown by Table 2, aminothiols (e.g., PrC-210 and PrC-211) provided radioprotection when administered via intraperitoneal and/or oral routes. In particular, PrC-210 and PrC-211 conferred radioprotection at doses less than the MTD.

Doses expressed as a fraction of "MTD" are expressed as a fraction of the "maximum tolerated dose". Doses expressed in units of ug/g correspond to micrograms of the compound per gram of body weight.

Scheme 1.

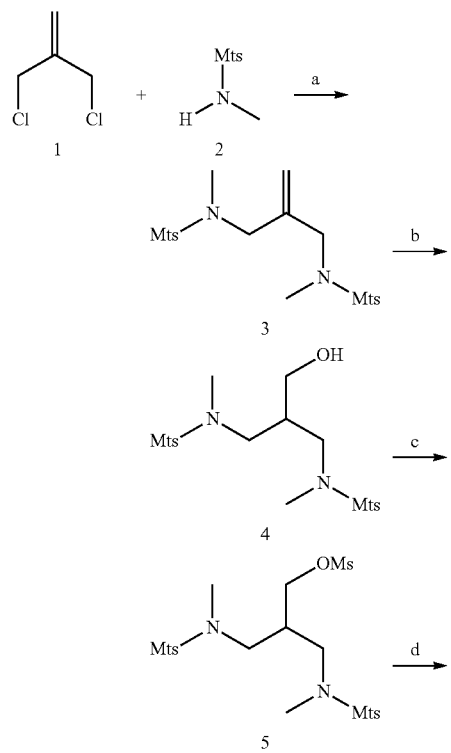

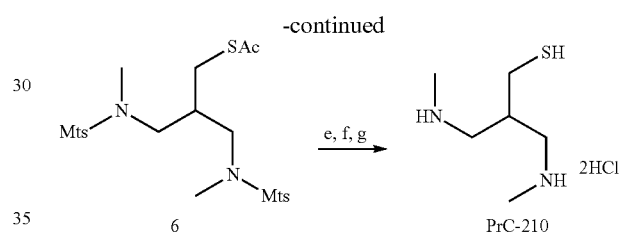

Reagents:
a NaH, DMF, THF;
b THF; EtOH, $H_2O_2$, NaOH (aq);
c MsCl, $Et_3N$, $CH_2Cl_2$;
d KSAc, DMF;
e HBr, PhOH, HOAc, $CH_2Cl_2$;
f $K_2CO_3$ (aq);
g HCl (aq), 2-mercaptoethanol, EtOH; recrystallize.
Mts = mesitylenesulfonyl Scheme 2.

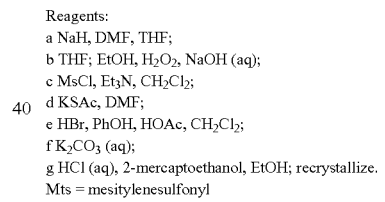

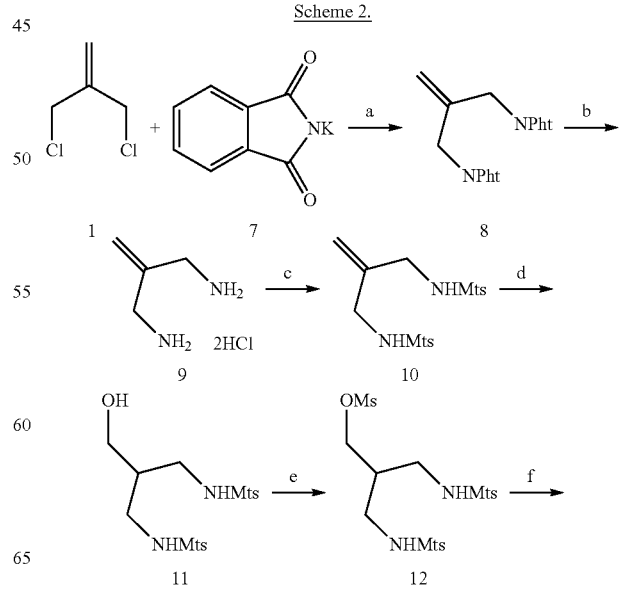

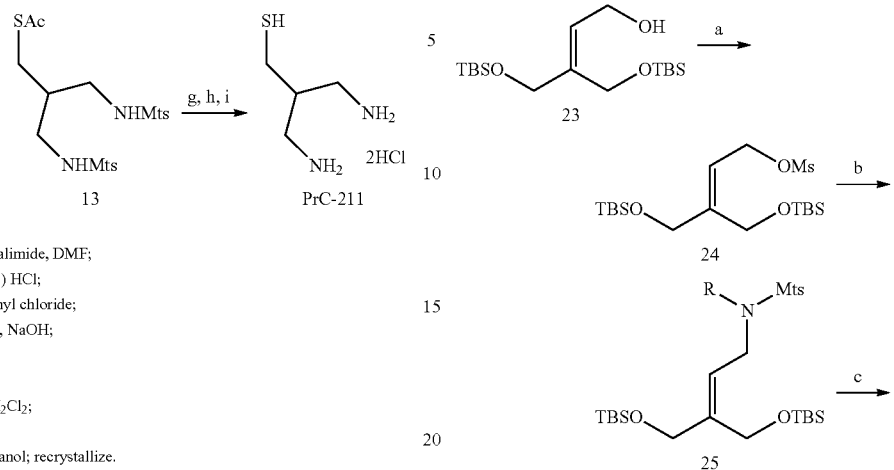

Reagents:
a 2 equiv. potassium phthalimide, DMF;
b (1) NH$_2$NH$_2$—H$_2$O, (2) HCl;
c NaOH, mesitylenesulfonyl chloride;
d (1) BH$_3$-THF, (2) H$_2$O$_2$, NaOH;
e MsCl, Et$_3$N, CH$_2$Cl$_2$;
f KSAc, DMF;
g HBr, PhOH, HOAc, CH$_2$Cl$_2$;
h K$_2$CO$_3$ (aq);
i HCl (aq), 2-mercaptoethanol; recrystallize.

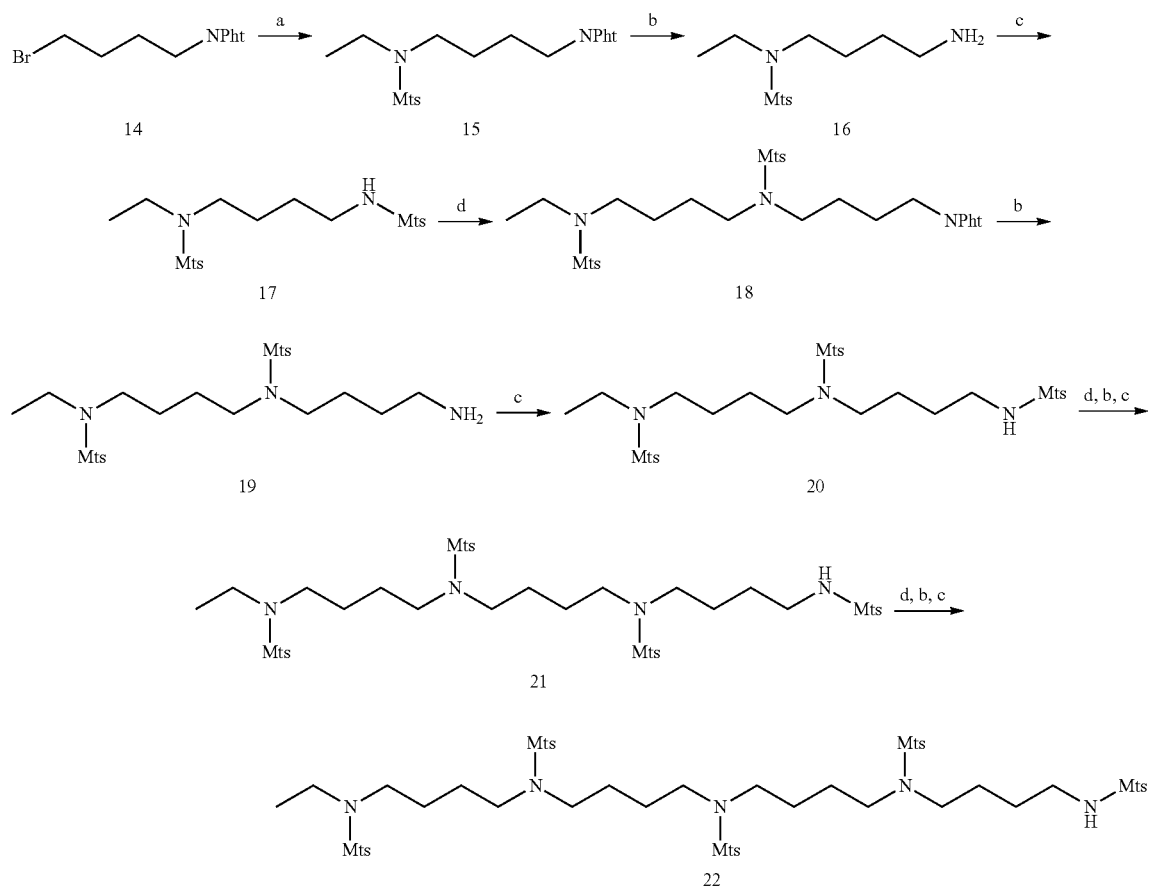

Reagents and conditions:
a N-ethyl mesitylenesulfonamide, NaH, DMF;
b N$_2$H$_4$—H$_2$O;
c mesitylenesulfonyl chloride, Et$_3$N, CH$_2$Cl$_2$;
d 4-bromobutylphthalimide, NaH, DMF

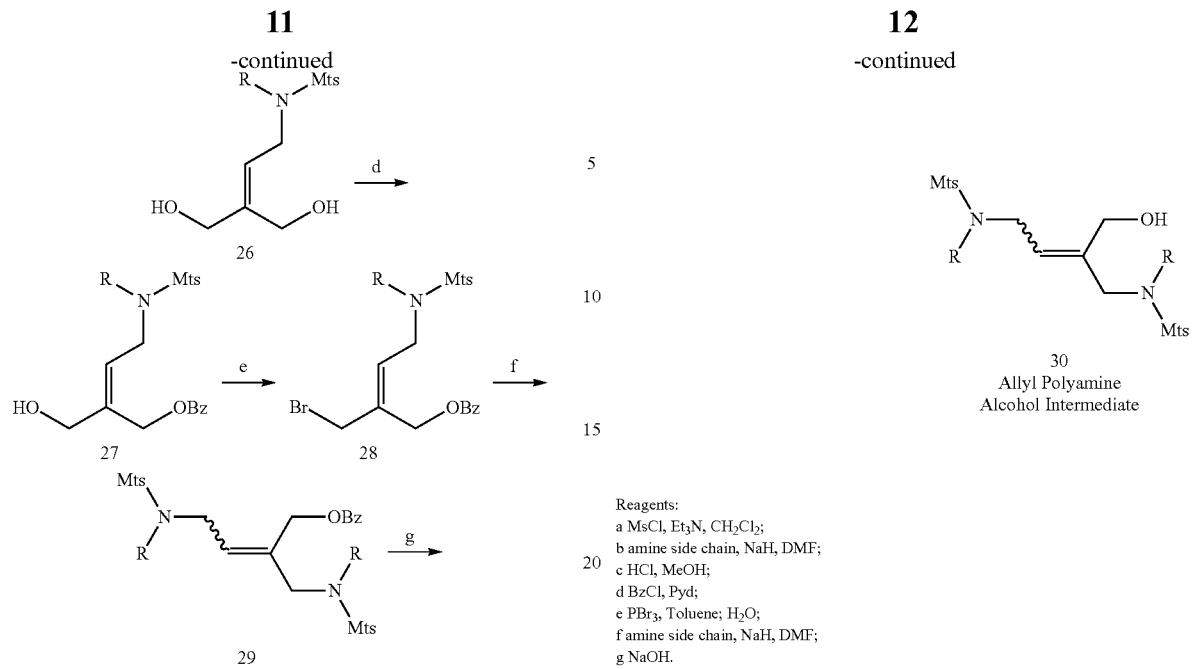
Reagents:
a MsCl, Et₃N, CH₂Cl₂;
b amine side chain, NaH, DMF;
c HCl, MeOH;
d BzCl, Pyd;
e PBr₃, Toluene; H₂O;
f amine side chain, NaH, DMF;
g NaOH.
Scheme 5.
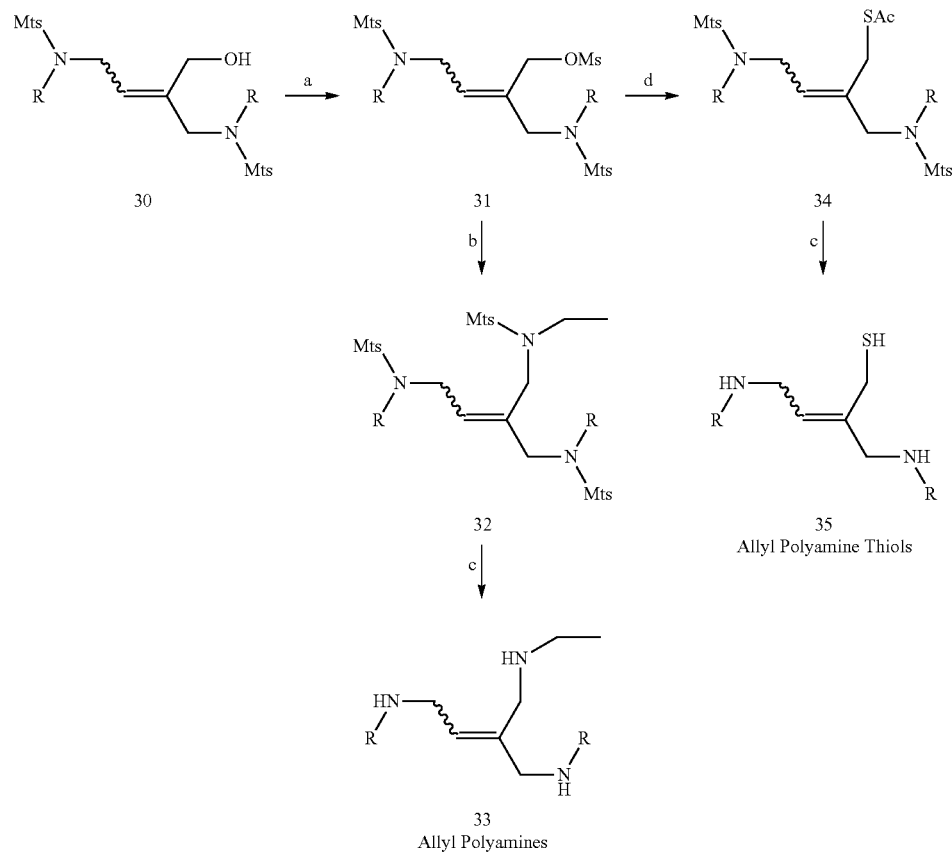
Reagents:
a MsCl, Et₃N, CH₂Cl₂;
b N-Et mesitylenesulfonamide, NaH, DMF;
c HBr, PhOH, HOAc, CH₂Cl₂; K₂CO₃ (aq); HCl (aq);
d KSAc, DMF.

I claim:

1. A method for protecting a subject from ionizing radiation, the method comprising:

administering systemically to a subject in need thereof an amount of a radioprotector compound comprising a free thiol and a positively-charged backbone, the radioprotector compound comprising a structure according to:

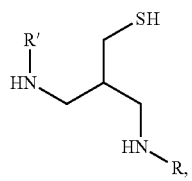

wherein R and R' are independently selected from H, $CH_3$, alkyl, and heteroalkyl;

wherein the amount is effective to protect the subject from ionizing radiation;

wherein systemic administration of the radioprotector compound to the subject is accomplished by intraperitoneal injection or intravenous injection.

2. The method of claim 1 wherein administering systemically to the subject the radioprotector compound does not cause a side effect of nausea, vomiting, hypotension, or fainting in the subject.

3. The method of claim 1 wherein the amount administered is effective to block cell cycle progression at the G1/S cell cycle border.

4. The method of claim 1 wherein the radioprotector compound is sulfurous odor-free.

5. The method of claim 1 wherein the amount administered is effective to inhibit the growth of a cell.

6. The method of claim 1 wherein the amount administered is effective to permit restoration of cell cycle progression.

7. The method of claim 1 wherein the amount administered is effective to bind the positively-charged backbone to a DNA while displaying the free thiol away from the DNA.

8. The method of claim 1 wherein the amount administered is effective to scavenge reactive oxygen species.

9. The method of claim 1 wherein the subject is a mammal.

10. The method of claim 1 wherein the subject is a human.

11. The method of claim 1 wherein the subject is a human comprising a cell exposed to radiation for medical purposes.

12. The method of claim 1 wherein an effective amount of the radioprotector compound is administered systemically at an effective time before or after radiation exposure.

13. The method of claim 1 wherein the systemic administration of the radioprotector compound to the subject is accomplished by intraperitoneal injection.

14. The method of claim 1 wherein the systemic administration of the radioprotector compound to the subject is accomplished by intravenous injection.

* * * * *